United States Patent [19]

Weiss et al.

[11] 4,118,099
[45] Oct. 3, 1978

[54] IMAGE CODING AND DECODING USING COHERENT CODES

[75] Inventors: Hermann Weiss, Hamburg; Erhard Klotz, Halstenbek; Ulf Tiemens, Pinneberg, all of Fed. Rep. of Germany

[73] Assignee: U.S. Philips Corporation, New York, N.Y.

[21] Appl. No.: 711,712

[22] Filed: Aug. 5, 1976

[30] Foreign Application Priority Data

Aug. 8, 1975 [DE] Fed. Rep. of Germany ....... 2535408
Nov. 29, 1975 [DE] Fed. Rep. of Germany ....... 2553869

[51] Int. Cl.² ............................................. G02B 27/00
[52] U.S. Cl. ............................. 350/3.73; 350/162 SF
[58] Field of Search .......................... 350/3.5, 162 SF; 250/313

[56] References Cited

U.S. PATENT DOCUMENTS 4,023,037  5/1977  Weiss et al. ....................... 350/3.5 X

OTHER PUBLICATIONS

Tipton et al., "Coded Aperture Imaging with On-Axis Fresnel Zone Plates", *Optical Engineering*, vol. 12, No. 5, Sep./Oct. 1973, pp. 166-168.
Weiss, "3-Dimensional X-Ray Information Retrieving...", 1974 *Intern. Optical Computing Conference*, Zurich, Switzerland, Apr. 1974, pp. 41-44.
Brown, "Multiplex Imaging with Multiple-Pinhole Cameras," *Journal of Applied Physics*, vol. 45, No. 4, Apr. 1974, pp. 1806-1811.
Kock et al., "Tomosynthesis:Holographic Methods...", 3rd Inter. Conf. on Medical Physics, Goteborg, Sweden, Jul./Aug. 1972.
Barrett et al., "Fresnel Zone Plate Imaging in Radiology...", *Optical Engineering*, vol. 12, No. 1, Jan./Feb. 1973, pp. 8-12.
Rogers et al., "Imaging... with Incoherent Holography", *Optical Engineering*, vol. 12, No. 1, Jan./Feb. 1973, pp. 13-22.
Wouters et al., "Direct Method of Decoding Multiple Images," *Applied Optics*, vol. 12, No. 8, Aug. 1973, pp. 1871-1873.

*Primary Examiner*—John K. Corbin
*Assistant Examiner*—John D. Lee
*Attorney, Agent, or Firm*—Frank R. Trifari; Simon L. Cohen

[57] ABSTRACT

A method of imaging a three-dimensional object with the aid of coding and decoding using coherent point codes, whereby the object is recorded in two steps, each with a plurality of radiation sources of different orientation on the same recording material.

Negatives of the two images are produced, after which the positive of one image is combined with the negative of the other image, the combined images being subsequently multiplied by means of point holograms formed with the aid of a reference wave and a multiplicity of light sources whose co-ordinates correspond to those of the point images of the two source arrays recorded by a pinhole camera, the two multiplied images being superposed in one plane, the coded images being decoded by changing their scale with the aid of two synchronously controlled zoom lenses whereby the coordinates of the point image function of an image of an object layer in the coded images are adapted to the points stored in the two point holograms.

6 Claims, 8 Drawing Figures

IMAGE CODING AND DECODING USING COHERENT CODES

The invention relates to a method of imaging a three-dimensional object with the aid of coding and decoding using coherent point codes, whereby the object is recorded in two steps, each with a plurality of radiation sources of different orientation on the same recording material.

It is known that image coding for three-dimensional objects can be achieved by exposure of the object to incoherent light or to X-rays from different directions and by photographically recording the shadow images on one and the same film. Thus, a superposition image is obtained from which the object information cannot be recovered directly. Only after a second step, to wit the decoding of the superposition image, can the different layers of the three-dimensional object be rendered visible and can discrete cross-sections of this object be reproduced. The actual decoding process can be performed in an incoherent optical multiplier arrangement, for example as proposed in the German Patent Application No. P 24 32 595.9. During the decoding based on the specific arrangement of the radiation sources in accordance with a non-redundant point configuration, undesired secondary images may be formed in which the signal-to-noise ratio fails to reach a specific threshold value. A publication by C. Brown in the "Journal of Applied Physics", Vol. 45, 1974, pages 1806–1811 describes how the signal-to-noise ratio can be improved for this method of image coding using coherent codes. An object is then recorded twice using two pinhole cameras with different aperture arrays, the image information being subsequently applied to a computer — negative values being assigned to one image and positive values to the other image and vice versa. The image can then be decoded with the computer. This computing process is impracticable for X-ray exposures, because of the large number of image points (up to $10^8$ image points).

It is an object of the invention to provide a simplified method of reproducing an image of a layer of a three-dimensional object.

This object is achieved in that negatives of the two images are produced, after which the positive of one image is combined with the negative of the other image, the combined images being subsequently multiplied by means of point holograms formed with the aid of a reference wave and a multiplicity of light sources whose co-ordinates correspond to those of the point images of the two source arrays recorded by a pinhole camera, the two multiplied images being superposed in one plane, the coded images being decoded by changing their scale with the aid of two synchronously controlled zoom lenses, whereby the co-ordinates of the point image function of an image of an object layer in the coded images are adapted to the points stored in the two point holograms.

Instead of the optical array an analog electronic array may be used. Decoding is then effected by correspondingly shifting the two coded images together with their negatives on an electronic storage tube.

The formation of the decoded image may then be explained as follows. When a suitable code is used of $n_1$ sources for the first exposure and $n_2$ sources for the second exposure decoding yields an image based on the amplitude $n = n_1 + n_2$, the N undesired secondary images ($N = n(n-1)$) being partly compensated for by the negatives of the two coded images, so that now less secondary images are produced, and thus the signal-to-noise ratio is substantially improved.

The method is in particular applicable in medical X-ray imaging, notably for the imaging of moving three-dimensional objects such as a beating heart into which a contrast medium has been injected. The heart is flashed twice within a very short time by means of a multiplicity of X-ray sources located at different positions and illuminating two separate films. After development of the films, decoding for imaging the different layers is effected by means of the method in accordance with the invention. Instead of a film an image intensifier may be used. Alternatively, decoding may be effected with an electronic shifting system as proposed in German Patent Application No. P 24 31 700.8.

An even simpler method of multi-layer reproduction is obtained in that the two superposition images are separated by means of a grating, but are recorded on a record carrier in a grating-like multiplexed manner, a negative of this image being made and the superposition images contained in the positive and the negative being spatially separated by way of a second grating and the positive of the one image being combined with the negative of the other image, the two resulting combined images being multiplied with the aid of two point holograms stored on a photographic plate, the said holograms being made with the aid of a reference wave and a multiplicity of light sources whose co-ordinates correspond to the point images of the two source arrays recorded by means of a pinhole camera, the two multiplied images being superposed as described hereinbefore.

Since the two coded superposition images are consecutively recorded on a single film using a 50% strip grating which is located near the film, said grating being shifted between the two exposures by one grating width, the position of the object relative to the film is fixed, so that only one film is needed, of which a negative is made, for example, by contact printing. The time between the exposures can be a few milliseconds (depending on velocity of the grating movement), and no film changing means is needed.

The combined images can be derived from the multiplexed image and the negative obtained by contact-printing by means of a 50% grating arrangement, so that the two superposition images on one film can be separated in a simple manner. Owing to the fixed lens arrangement and stable recording geometry, moving the grating by one grating width enables arbitrary combinations to be made and simplifies the alignment of the images to be added to each other.

As the two combined images are multiplied by means of two point holograms recorded on a single photographic plate, and because the images are transmitted by a single lens, alignment of the holograms and the lenses is no longer necessary, so that recording of the holograms is simplified.

Some embodiments of the invention will be described in more detail with reference to the drawing, in which.

Figure 1:
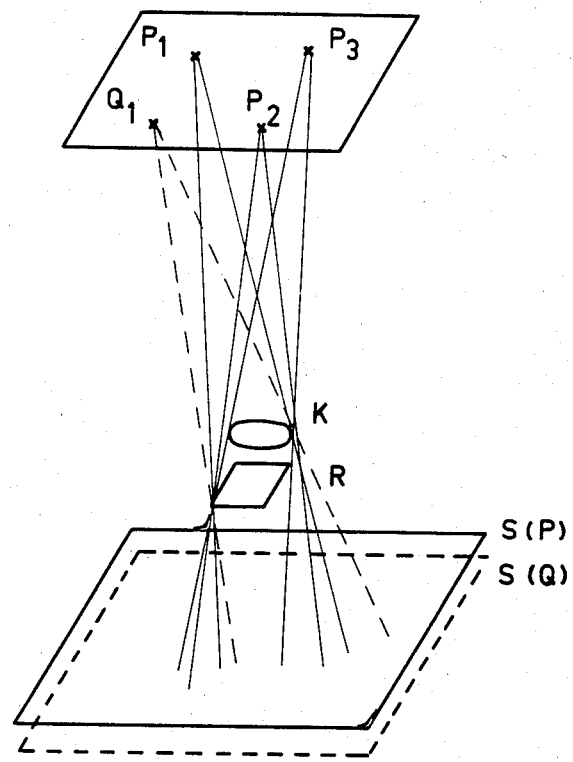
FIG. 1 shows the image coding of an object.
Figures 2A, 2B:
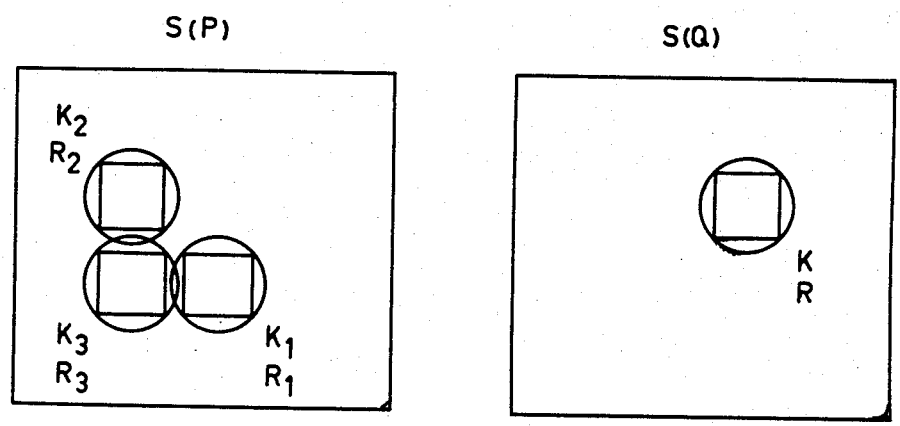
FIGS. 2a and 2b show the coded images of the object.

The coding and decoding principle will be described on the basis of a simplified system using four radiation sources $P_1$, $P_2$, $P_3$, $Q_1$. FIG. 1 illustrates the process of recording a three-dimensional object consisting of a circle K and a square R situated in different planes. Two exposures are made: first the sources $P_1$, $P_2$, $P_3$ simultaneously irradiate the object, yielding a coded image S(P). Directly after this, the source $Q_1$ irradiates the object, yielding an image S(Q). Generally speaking, $n_1$ sources $P_1 \ldots P_{n1}$ are provided for the first exposure and $n_2$ sources $Q_1 \ldots Q_{n2}$ for the second exposure. The arrangement of the $n = n_1 + n_2$ sources determines the decoding, which will be described hereinafter. The sources of the category Q are also referred to as "negative sources" and those of the category P as "positive sources". The term "coherent coding" can alternatively be used for this method. FIG. 2a shows the two coded images S(P) recorded with the positive sources, and FIG. 2b the images S(Q) recorded with the, in this case, single negative source. These two coded images, containing the circles $K_1$, $K_2$, $K_3$; K and the squares $R_1$, $R_2$, $R_3$; R, obtained by irradiation by the sources $P_1$, $P_2$, $P_3$ and $Q_1$, respectively, are employed for decoding. The coded images may also be displayed on an image intensifier tube.

The formula in accordance with which the decoded object S" is reconstructed from the coded images S(P), S(Q) and their negatives S(P) and S(Q), is given by:

$$S'' = \underbrace{\underbrace{([S(P) - S(Q)])}_{a_1} \circledast P}_{b_1} + \underbrace{\underbrace{([S(Q) - S(P)]}_{a_2} \circledast Q}_{b_2}$$

$$\underbrace{\phantom{xxxxxxxxxxxxxxxxxxxxxxxxxxxxxxxxxxxxxxxxx}}_{c}$$

The functions P and Q are the point-image functions of the exposures with the sources $P_i$ and $Q_i$ respectively; the sign ⊛ denotes mathematical correlation and in the present instance merely represents a shift and addition of images owing to the simple point image functions P and Q which consist of three points and one point, respectively. The mathematical process is divided into the steps $a_1$, $a_2$, $b_1$, $b_2$, c represented in FIGS. 3 through 5. For the sake of simplicity, the decoding is only described for the plane of the square R; for the plane of the circle K the decoding is effected in a similar way, except for the changed scale of the coded images.

Figure 3A:
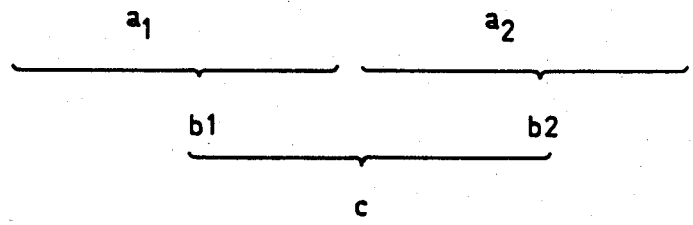
FIGS. 3a and 3b show two coded intermediate images.
Figure 3B:
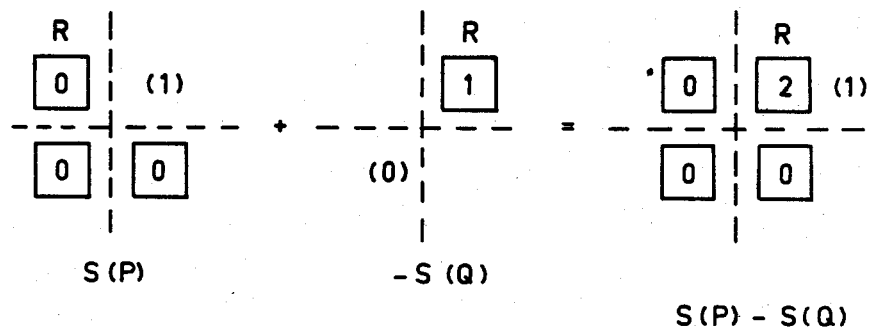
Figure 4:
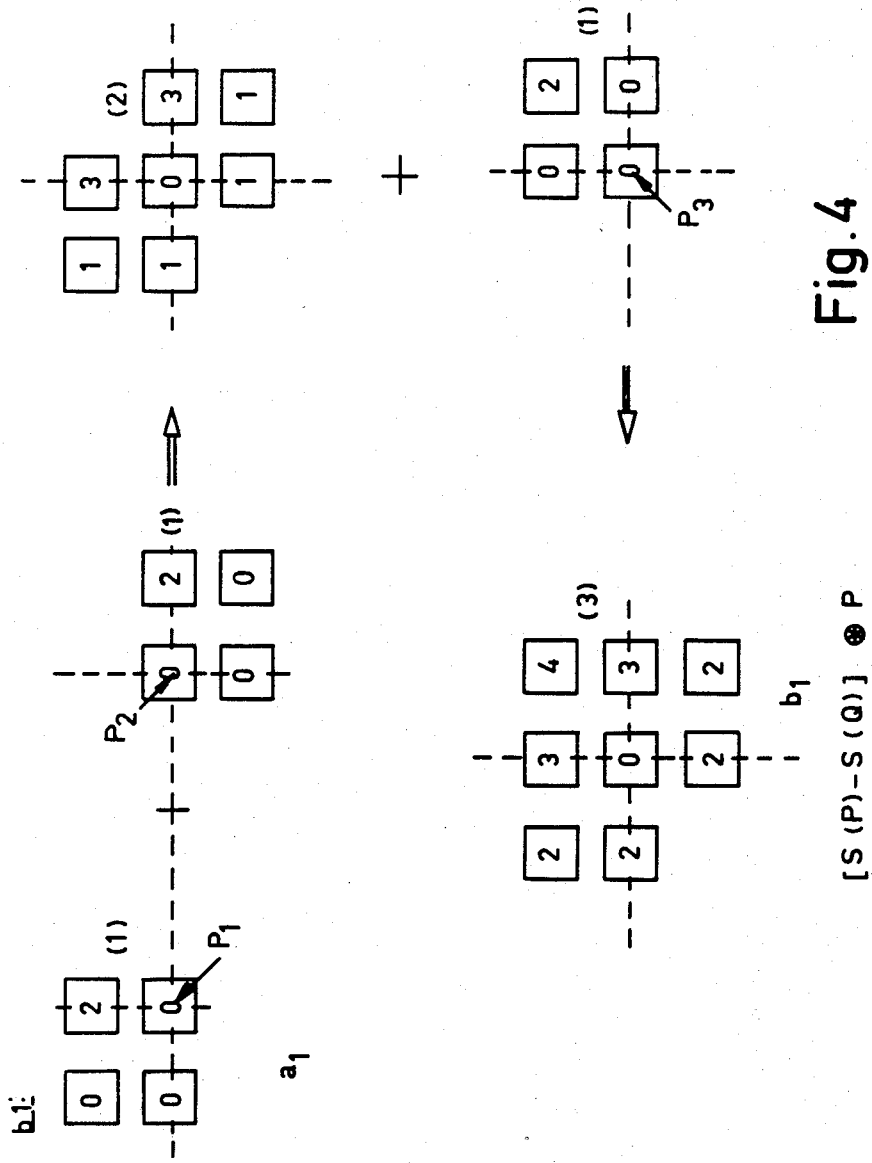
FIG. 4 shows the first multiplying step.
Figure 5:
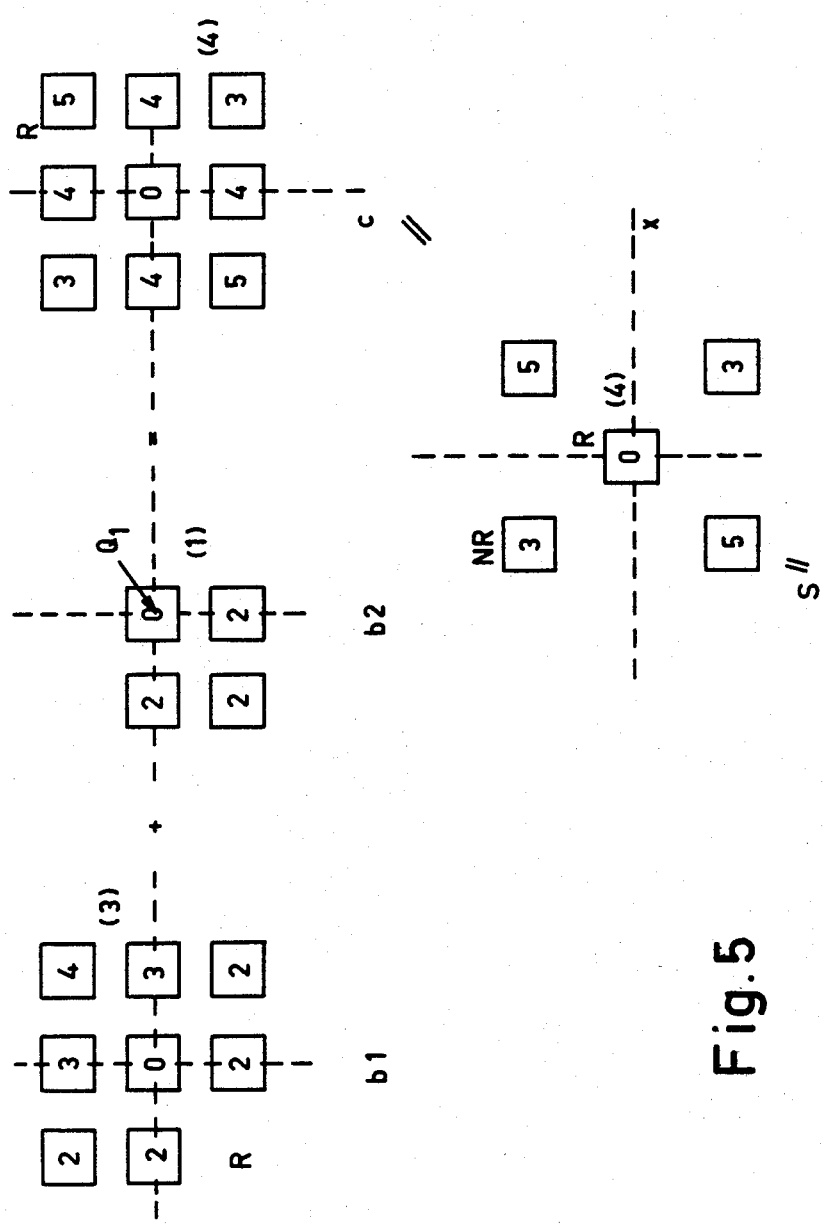
FIG. 5 shows the second multiplying step of the decoding process.

FIG. 3a represents step $a_1$. During step $a_1$ an image is formed by adding the coded image S(P) and the negative −S(Q) of the coded image S(Q): the square R in the image S(P) will then have a density 0 and the surrounding area the density (1), which is also the case in the image S(Q) in FIG. 3b; the negative −S(Q) in FIG. 3a then has a density 1 in the square R and a density (0) in the surrounding area. The sum of the two, S(P) − S(Q), then has a density (1) in the surrounding area and the densities 0,0,0,2 the 4 squares R. During the step $a_2$ (FIG. 3b) a corresponding image S(Q)-S(P) is obtained by adding S(Q) and the negative −S(P). FIGS. 4 and 5 illustrate the decoding of the square R on the basis of the images S(P)−S(Q) and S(Q)−S(P). During step $b_1$ the image $a_1$ is tripled and the three resultant identical images are shifted relative to each other in accordance with the vectors $P_1$, $P_2$ and $P_3$ of the image point function P and added to each other. The resulting image S(P)–S(Q) ⊛P then consists of 8 squares of the density 0, 2, 3, 4 and background density (3). Referring to FIG. 5, the image $b_1$ and the image $b_2$, produced by shifting the image S(Q)-S(P) about the vector $Q_1$ of the image point function Q, are now added, yielding the image c. The image c is identical to the decoded image S", which consists of a square R of the density 0 in the center, which is in contrast with the surrounding area of density (4). Moreover, four secondary squares NR of the density 3 and 5 are present, which represent the background or "noise" of the image, whereas the center square R is the decoded square which represents the "signal". Accordingly, the contrast ratio of 4:1 between "signal" and background amounts to n:1 when $n = n_1 + n_2$ sources are used. In this respect it is of importance to find such arrangements of positive sources $P_i$ and negative sources $Q_i$ that in the decoded image the density of the secondary images only differs by ± 1 from the density of the background. Such arrangements are sometimes referred to as "non-redundant coherent ± codes". When only incoherent non-redundant arrangements are used, always $n(n-1)$ secondary images are obtained. In the case of an incoherent source arrangement comprising 4 sources, there are consequently $n = 4.3 = 12$ secondary images, whereas in the case of the coherent code with +1, +1, +1 and −1, only 4 secondary images are produced. This clearly illustrates the advantage of coherent codes. However, two exposures have to be made of the object, the positive sources being assigned to the first exposure and the negative source to the second exposure.

Figure 6:
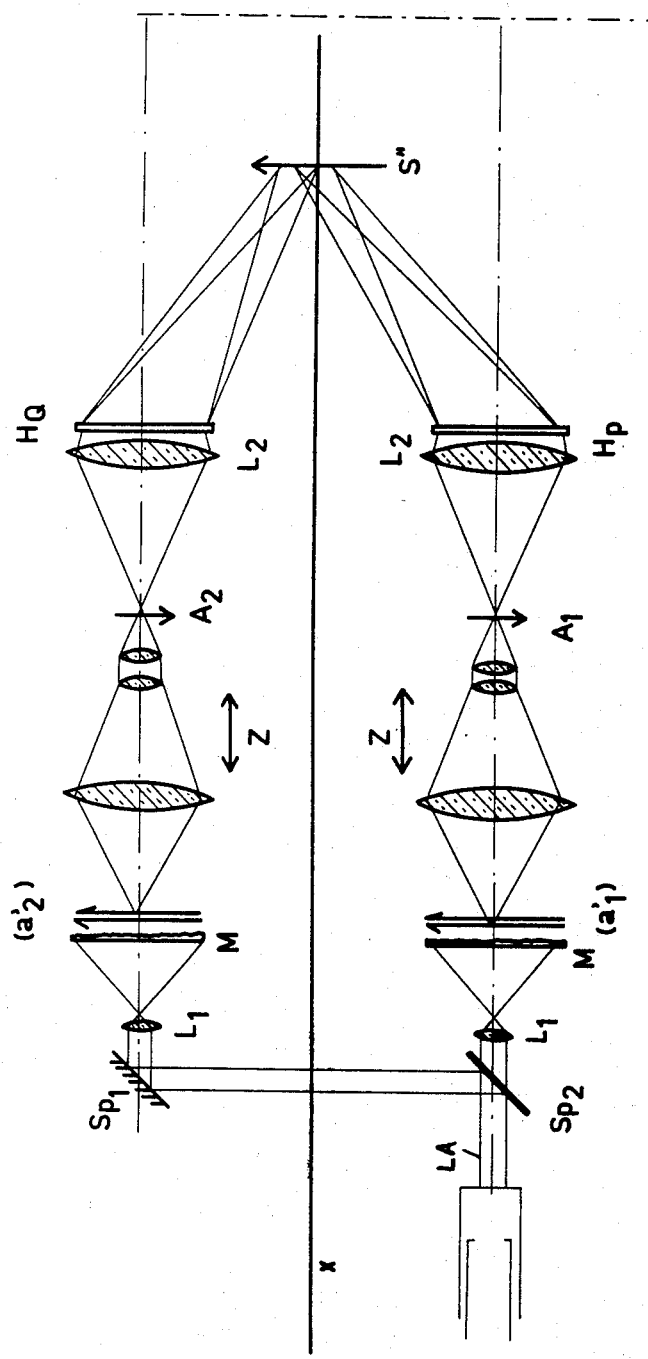
FIG. 6 shows an optical system for decoding images of three-dimensional objects.

FIG. 6 shows an optical system by means of which the decoding principle described with reference to FIGS. 3-5 can simply be realized. The system comprises two units. A laser beam LA which may be monochromatic but spatially incoherent, is split into two beams by a semitransparent mirror $Sp_2$ and a mirror $Sp_1$. Each beam is diverged by lenses $L_1$ and illuminates ground-glass screens M. Behind the screens images $(a'_1)$ and $(a'_2)$ are formed as described previously: $(a'_1)$ consists of the image S(P) and the negative of the image S(Q), while $(a'_2)$ consist of the image S(Q) and the negative of the image S(P). By means of zoom lenses Z the scale of these images can be changed. The intermediate images $A_1$ and $A_2$ thus obtained are multiplied with the aid of the lenses $L_2$ and the holograms $H_P$ and $H_Q$ (steps $b_1$ and $b_2$) and added in an image plane so as to obtain the reconstructed image S" (step c). The hologram $H_P$ contains the image point function P and the hologram $H_Q$ contains the image point function Q. These are so-termed point or multiplication holograms. The decoded image S" can then be observed directly.

For different layers of the object decoding is possible by simultaneously moving the two zoom lenses so as to obtain a parallel change in scale of the intermediate images $A_1$ and $A_2$.

Instead of the positives and negatives of the images $(a'_1)$ and $(a'_2)$, two electron-optical transducers such as, for example, photo-titus tubes may be employed, onto whose targets the positives are flashed, while during a second flash the voltage is reversed, yielding negatives.

Alternatively, the steps $a_1$, $a_2$, $b_1$, $b_2$, c can be realized by using an electronic storage tube, in which the positives (bright-dark) and negatives (dark-bright) can be stored and added. Starting from the two images S(P)

and S(Q) the sequence of shifting and summation is fully arbitrary.

What is claimed is:

1. A method of imaging a three-dimensional object with the aid of coding and decoding using coherent point codes, comprising recording the object with a plurality of radiation sources of different orientations on a recording medium, recording the object again separately with a second plurality of differently oriented radiation sources, forming the negatives of the two recorded images, separately combining the positive of each recorded image with the negative of the other image, to form two combined images, multiplying the combined images by means of point holograms formed with the aid of a reference wave and a multiplicity of light sources whose co-ordinates correspond to those of the point images of the two source arrays recorded by a pinhole camera, superimposing the two multiplied images in one plane, and decoding the coded images by changing their scale with the aid of two synchronously controlled zoom lenses whereby the co-ordinates of the point image function of an image of an object layer in the coded images are adapted to the points stored in the two point holograms.

2. A method as claimed in claim 1, wherein the two coded images are obtained by X-ray flashes on two separate films from different directions, and that the negatives are made by contact printing.

3. A method as claimed in claim 2, wherein the information contained in the X-ray images is displayed on an electron-optical image transducer and the negatives are made by reversing the polarity of the information signal of the transducer.

4. A method as claimed in claim 1, wherein the two coded images are decoded by correspondingly shifting and adding the positives and negatives on an electronic storage tube by bright-dark and dark-bright scanning, respectively.

5. A method as claimed in claim 1 characterized in that the coded images are displayed on an image intensifier tube.

6. An improved method of imaging a three-dimensional object with the aid of coding and decoding using coherent point codes, whereby the object is recorded in two steps, each with a plurality of radiation sources of different orientation on the same recording material, the improvement wherein the two superposition images are separated by means of a grating, but are recorded on a record carrier in a grating-like multiplexed manner as a multiplexed image, a negative of this multiplexed image being made and the superposition images contained in the positive and the negative being spatially separated by way of a second grating and the positive of the one image being separately combined with the negative of the other image forming two combined images, the two resulting combined images being multiplied with the aid of two point holograms stored on a photographic plate, the said holograms being made with the aid of a reference wave and a multiplicity of light sources whose co-ordinates correspond to the point images of the two source arrays recorded by means of a pinhole camera.

* * * * *